United States Patent

Brunke et al.

[11] Patent Number: 5,711,939
[45] Date of Patent: Jan. 27, 1998

[54] USE OF ESTERS OF BRANCH-CHAIN CARBOXYLIC ACIDS WITH BRANCH-CHAIN ALCOHOLS AS INGREDIENTS OF COSMETIC AGENTS

[75] Inventors: Ernst-Joachim Brunke; Willi Rojahn; Gerhard Spirik, all of Holzminden, Germany

[73] Assignee: Dragoco Gerberding & Co., GmbH, Germany

[21] Appl. No.: 529,930

[22] Filed: May 29, 1990

Related U.S. Application Data

[63] Continuation of Ser. No. 926,730, Mar. 20, 1986, which is a continuation of Ser. No. 589,107, Feb. 23, 1984, abandoned.

[30] Foreign Application Priority Data

Aug. 26, 1982 [DE] Germany ............... 3231704.2
Aug. 26, 1982 [DE] Germany ............... 3231705.0
Aug. 26, 1982 [DE] Germany ............... 3231706.2

[51] Int. Cl.⁶ .................................................. A61K 7/42
[52] U.S. Cl. ........................................ 424/59; 424/60
[58] Field of Search ................................ 424/59

[56] References Cited

U.S. PATENT DOCUMENTS

| | | | |
|---|---|---|---|
| 2,192,907 | 3/1940 | Harris | 424/70 |
| 3,809,652 | 5/1974 | Brennan | 560/265 X |
| 3,976,789 | 8/1976 | Tomita et al. | 424/59 |

FOREIGN PATENT DOCUMENTS

| | | | |
|---|---|---|---|
| 0062896 | 10/1982 | European Pat. Off. | 424/59 |
| 1486689 | 5/1967 | France | 560/265 |
| 0017136 | 2/1979 | Japan | 424/70 |
| 0015406 | 2/1980 | Japan | 424/70 |
| 0102510 | 8/1980 | Japan | 424/70 |
| 0053402 | 3/1982 | Japan | 424/70 |

OTHER PUBLICATIONS

Kidder et al., Industrial & Engineering Chemistry, 1947, vol. 39, pp. 484 to 491.

Jellinek, Cosmetics & Toiletries, Mar. 1978, vol. 93, pp. 69, 70 and 72.

*Primary Examiner*—Shelley A. Dodson
*Attorney, Agent, or Firm*—Hedman, Gibson & Costigan, P.C.

[57] ABSTRACT

The invention comprises the use of multiple-branch esters of the common formula A, formed from branch-chain carboxylic acids and branch-chain alcohols, as ingredients of cosmetic agents for the protection and care of human skin

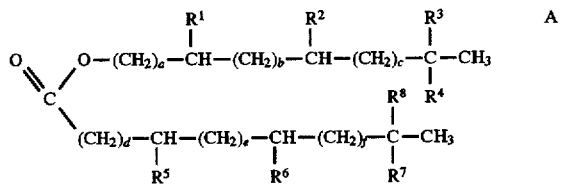

$R^1, R^2, R^3, R^4, R^5, R^6, R^7, R^8 = H, Me, Et$ $a + b + c = 4\text{--}14$ $d + e + f = 4\text{--}14$ as well as cosmetic agents containing such branched esters of common formula A.

1 Claim, No Drawings

USE OF ESTERS OF BRANCH-CHAIN CARBOXYLIC ACIDS WITH BRANCH-CHAIN ALCOHOLS AS INGREDIENTS OF COSMETIC AGENTS

This is a continuation application of U.S. patent application Ser. No. 06/926,730, filed Mar. 20, 1986; which is a continuation application of U.S. patent application Ser. No. 06/589,107, filed Feb. 23, 1984, now abandoned.

DESCRIPTION

Cosmetic products for the care of human skin consist of a base incorporating the special reagent chosen for the specific use being considered. In these bases different active materials and perfume oils can be incorporated. Cosmetic bases should not only be carriers for the active materials but should themselves also exert the greatest possible positive effect on the skin, for example, to protect the skin surface against external damage and to exert a balanced influence on the moisture- and fat content of the skin.

The creams and lotions commonly used in cosmetics are emulsions of hydrocarbons, fats, natural or synthetic waxes, emulsifiers and water. The consistency of the emulsion and skin effect depend upon the nature and the concentration of the ingredients. It has been shown that for a cosmetic product as high a water-vapor permeability as possible is desirable, that does not impair the normal skin function. Natural fats used in large amounts are often triglycerides of straight-chain fatty acids (e.g. stearic- and palmitic acids). Such high molecular triglycerides hinder the passage of water vapor through the skin; the branch-chain analogs have herein clearly better properties (G. Weitzel et al., Hoppe-Seyler'Zeitschrift. Physiol. Chemie, 301, 26 (1955)).

Accordingly different branch-chain compounds were developed for the cosmetic industry, (hydrocarbons, carbonic acids, alcohols and esters), used for the raising of the spreadability of the cosmetics (review in: M. G. de Navarre, American Perfumer and Cosmetics, 79 (1963)). The effect of branch-chain esters in skin-care products was discovered as a special advantage (J. S. Jellinek, Cosmetics and Toiletries 95, 69 (1978)).

At present one of the efficient products in this group has proved to be "PCL-liquid (A. Berg, DRAGOCO-Report, 159 (1976). These behave essentially as compounds 1a,b, a mixture of esters of 2-ethyl-hexanoic acid and the straight-chain $C_{16}/C_{18}$ -n-alcohols.

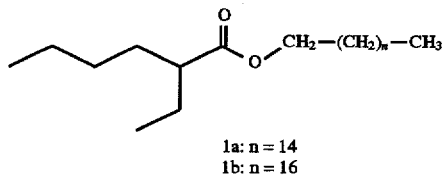

1a: n = 14
1b: n = 16

It is the object of the present invention to improve the properties of cosmetics by the use of new substances or of those chemically known substances whose suitability for cosmetic preparations was not yet known.

Especially shall the water-vapor permeability of skin cosmetics be improved by the use of substances not hitherto included for such uses and the even dispersion of the active material over the skin made possible.

It is a further object of the present invention to provide new cosmetic agents showing improved properties because of their content of substances not used hitherto in cosmetics.

These objects are achieved by the use of the substances to which the patent claims are directed or of agents with a content of these substances.

The part-groups highlighted in particular sub-claims for the groups indicated in the main claim, comprise particularly suitable substances.

The present invention therefore relates to the use of substances of the common formula A or cosmetic agents containing an effective amount of such compounds A.

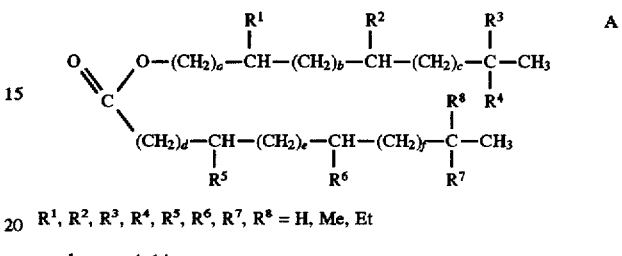

$R^1, R^2, R^3, R^4, R^5, R^6, R^7, R^8$ = H, Me, Et $a + b + c = 4–14$ $d + e + f = 4–14$

It has been found that substances of common formula A in accordance with the invention possess a high spreadability and also surpass the ester mixture 1a,b in this. The water-vapor permeability of cosmetics that contain compounds A is clearly improved on the skin. Moreover the compounds A impart to different cosmetic mixtures the property of spreading readily on the skin. Uniform distribution over the skin is convenient for applying a specific active agent (e.g. a light-screening substance) by a cosmetic.

The high spreadability of compounds of the common formula A can be seen in the series of various substitutions in the molecules. The alcohol- as well as the acid element is branch-chained. The substances of formula A at room temperature are liquids of medium viscosity and can easily be manipulated. Because of multiple branching and lack of unsaturation compounds A are oxidisable only with difficulty and accordingly show practically no rancidity. The esters of formula A can therefore be used advantageously, alone or in mixtures, as ingredients of cosmetic products. Skin oils (e.g. sun-screen oils) can contain up to 90% of esters of formula A. Because of the higher spreadability of compounds A larger amounts of paraffin oils can also be used in mixtures than would be otherwise desirable.

The dosage of esters A in cosmetic products preferably amounts to 2–30%.

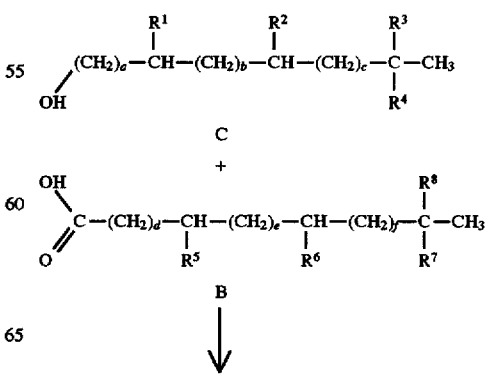

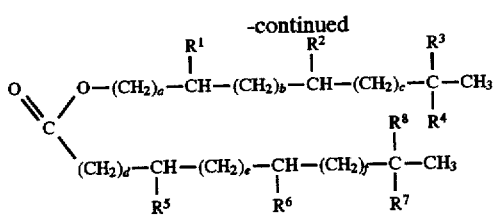

-continued

R¹, R², R³, R⁴, R⁵, R⁶, R⁷, R⁸ = H, Me, Et
a + b + c = 4–14
d + e + f = 4–14

In the esters of common formula A according to the invention, R¹, R², R³ and R⁴ or R⁵, R⁶, R⁷ and R⁸ cannot simultaneously be hydrogen atoms, which follows from the definition "branch-chain" for the alcohols as well as for the acids. The symbols a,b,c,d,e,f can each individually take any desired numerical value for 0 to 14, so long as the limit conditions a+b+c=4–14 or d+e+f=4–14 are met.

The preparation of the esters A is achieved by normal esterification of the corresponding branch-chain alcohols ant acids or by conversion of branch-chain alcohols with acid chlorides.

Different industrially produced single or multiple branched acids B (e.g. 2-ethylhexanoic acid, 3,5,5-trimethylhexanoic acid or isooctanoic acid) can be used as carboxylic acid and different industrially produced single or multiple branched alcohols C (e.g. 2-ethylhexanol, isooctanol isomers, isononanol, isodecanol isomers, isotridecanol isomers, isooctanedecanol isomers) as alcohols.

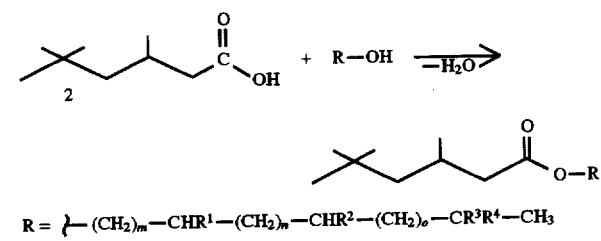

$R = \}{-}(CH_2)_m{-}CHR^1{-}(CH_2)_n{-}CHR^2{-}(CH_2)_o{-}CR^3R^4{-}CH_3$

R¹, R², R³, R⁴, R⁵, R⁶, R⁷, R⁸ = H, Me, Et
a + b + c = 4–14
d + e + f = 4–14 e.g. α-Ethylhexyl-
Isooctyl-(Isomers)
3,5,5-Trimethylhexyl-(Isononyl-)
Isodecyl-(Isomers)
Isotridecyl-(Isomers)
Isooctadecyl- The isononanoic acids (2) were obtained industrially by oxidation of the hydroformylation products of dimeric isobutylene and have a purity of about 90% (e.g. U.S. Pat. No. 2,470,859 or British patent 664,180). The by-products of these technical syntheses are constitutional isomers. The limited amounts of constitutionally isomeric esters present do not operate negatively against their use as cosmetics.

The branch-chain alcohols (R—OH) are in part products of the oxo-synthesis of olefin mixture and are present as mixtures of constitutional isomers (especially isooctanol, isodecanol and isotridecanol). A shift in the concentration of the multiple branched esters contained therein influences their use in cosmetics only trivially.

In German patent OLS 2 757 559 (published Jul. 5, 1979) the use of isonananoic acid esters as scent materials is described, in which the alcohol part contains 1–5 carbon atoms. The higher and branch-chain homologs or their use in skin-care agents was not known.

2-ethylhexanoic acids (3) and 2-ethylhexanol were produced industrially in large quantities and used in plastics. Of the higher esters of formula A of ethylhexanoic acid 2-ethyl hexanoic acid 2-ethyl hexyl ester is a known substance. It has f.i. been

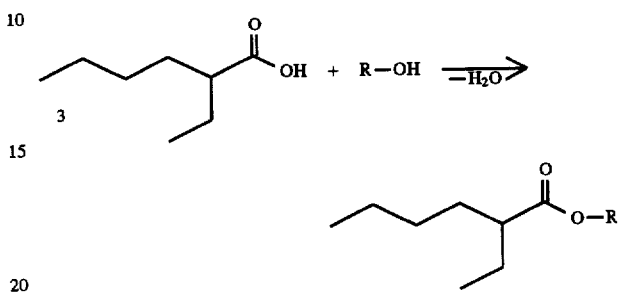

R¹, R², R³, R⁴, R⁵, R⁶, R⁷, R⁸ = H, Me, Et
a + b + c = 4–14
d + e + f = 4–14 e.g. α-Ethylhexyl-
Isooctyl-(Isomers)
3,5,5-Trimethylhexyl-(Isononyl-)
Isodecyl-(Isomers)
Isotridecyl-(Isomers)
Isooctadecylobtained as the by-products of the synthesis of 2-ethylhexanol from butyraldehyde (K. Nagaoka, T. Adachi and S. Rudo, Kogyo Kagaku Zasshi 66, 231, 1822 (1963). Netherlands application 510,136 (Feb. 7 1966) describes the suitability of this ester as agent for technical foam inhibiters. The production of this known ester can follow by normal acid-catalysed esterification of 2-ethylhexanoic acids (3) and 2-ethylhexanol, or by conversion of 2-ethylhexanol with the corresponding acid chloride. A further production method (use of molybdenum sulfide active charcoal) is described in U.S. Pat. No. 3,329,826 (Jul. 4, 1967) 2-ethylhexanoic acid-2-ethylhexyl ester can also be prepared by noble-metal catalysed partial oxidation of 2-ethylhexanol (French patent 1,563,259 of 11 Apr. 1969). In French application 2,282,467 (19 Mar. 1976) is claimed the use of these known esters as dielectric material for transformers. Further methods for the production of the ester are described by A. N. Shapolova, V. I. Lyubomilov, R. N. Sivkova and A. Kh. Bulai, Zh. Org. Khim. 1979, 2469 and by W. Tamura, Y. Kukenoka, Y. Suzuki and S. Yamamatsu, Jpn. Kokai Tokkyo Koho 80 22, (18 Feb. 1980).

Nothing was known about the suitability of the 2-ethylhexanoic acid-2-ethylhexylesters or the other higher branch-chain esters of 2-ethylhexanoic acid as cosmetics ingredients. It is therefore novel to use these esters as liquid waxes suitable for the compilation of cosmetic bases.

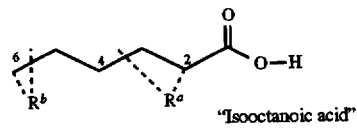

"Isooctanoic acid"

$R^a$: $CH_3$ alternatively at C-2, C-3 or C-4
$R^b$: $CH_3$ alternatively at C-5, C-6 or C-7
or C-6 + C-6

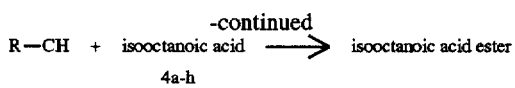

The "isooctanoic acid" (4) was prepared industrially by oxidation of "isooctylaldehyde", which further results from oxosynthesis of a heptene mixture (obtained by codimerisation of propylene and butylene) (see also: J. Falbe, "Syntheses with carbon monoxide", 1 chapter. "Hydroformylierungen" (Roelon reaction), Springer-Verlag, Berlin, Neidelberg, New York 1967; N. R. Kyle, "Oxo process", in: Kirk-Othmer, vol. 14, 2nd edition pp 373–390, J. Wiley & Sons, New York 1967). Correspondingly the "isooctanoic acid" occurs as a mixture of constitutional isomers. The normal variation of the relative concentration of the industrially prepared isomer composition has no significant effect on the favorable cosmetic properties of the isooctanoic acid-2-ethyl-hexyl-ester mixture. Based on the synthesis route, "isooctanoic acid" consists of the C-8 carboxylic acids 4a–h. Further methyl group changes are possible, but they play only a subordinate role. The mixture of methylesters 5a–h were prepared for investigation by mass spectroscopy.

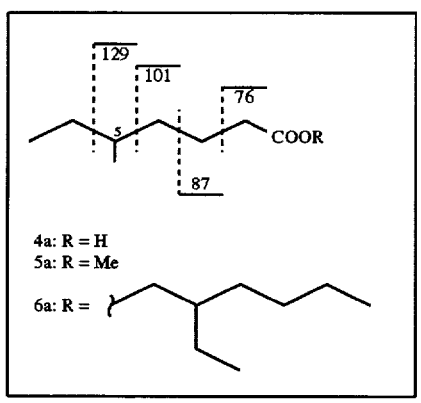
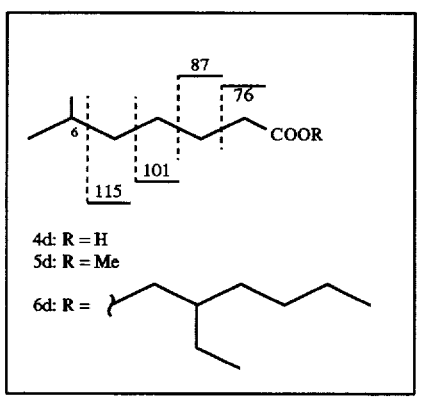
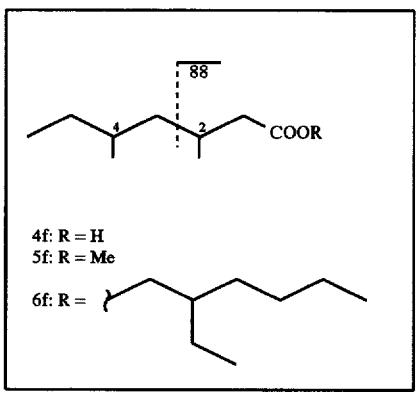
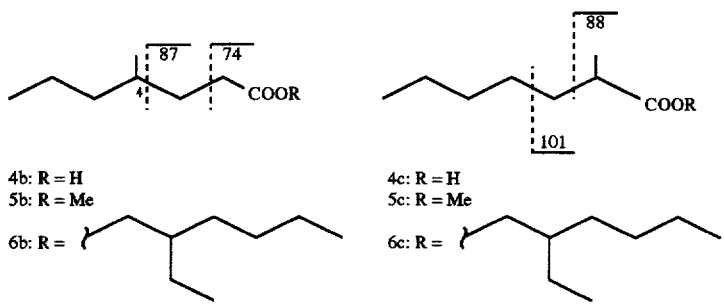
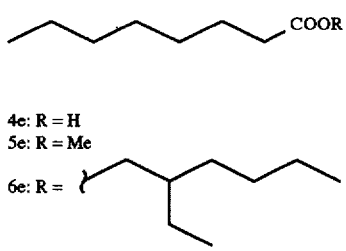
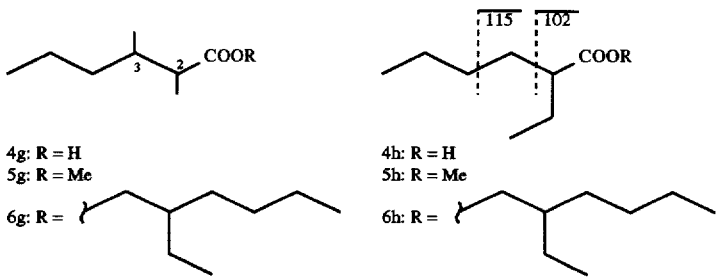

The correlations given in FIG. 1 were obtained from the above given mass spectrometric breakdown. These isomer distributions are repeated for the branch-chain esters of formula A, as can be shown by the example of the 2-ethylhexyl-esters 6a–h (gas chromatogram FIG. 2, mass spectra of the main isomer FIG. 3).

The relative composition of the branch-chain isooctanoic acid ester isomers of formula A can be subjected to the normal variation of large scale chemical processes without the use of the esters in cosmetic agents being impaired. By analogy with the directions given for 2-ethylhexanoicisononanoic- and isooctanoic acids, the branch-chain esters of higher homolog acids, such as isodecanoic-, isotridecanoic-, or isooctadecanoic acids can be prepared and used as ingredients of cosmetic products. The following examples explain the invention.

EXAMPLE 1

Preparation of 2-ethylhexanoic acid-3,5,5-trimethyl ester 2 g concentrated sulfuric acid were added to a solution of 144 g (1 mol) 2-ethylhexanoic acid and 144 g (1 mol) 3,5,5-trimethylhexanoic (isononyl alcohol) in 300 ml toluene and heated to boiling with water separation until the equimolar amount of water separates (about 2 hours). After cooling it was washed with water and then with 10% NaHCO$_3$ solution. The solvent was distilled off under reduced pressure. The remaining end-product after distillation over a 20 cm Vigreux column gave 220 g/(85%)2-ethylhexanoic acid ester as a colorless oil of medium viscosity.; B.P. (1 mm)=118°–120° C.

$d_4°^{20°}$: 0.8555 $n_D^{20°}$: 1.4346

EXAMPLE 2

Density and refraction of some 2-ethylhexanoic acid esters (preparation analogous to Example 1)
2-ethylhexanoic acid-isodecyl ester
(from isodecanol isomer mixture from Hoechst)
$d_4°^{20°}$: 0.8603 $n_D^{20°}$: 1.4382

2-ethylhexanoic acid-isotridecylester
(from tridecanol isomer mixture from Hoechst)
$d_4°^{20°}$: 0.8629 $n_D^{20°}$:1.4444

2-ethylhexanoic acid-isooctadecylester
$d_4°^{20°}$: 0.8569 $n_D^{20°}$: 1.4473

EXAMPLE 3

Preparation of 3,5,5-trimethylhexanoic acid-2'-ethylhexylester 2 g concentrated sulfuric acid were added to a solution of 130 g (1 mol) 2-ethylhexanol and 158 g (1 mol) 3,5,5-trimethyl hexanoic acid in 300 ml toluene and heated to boiling with water separation until the eqimolar amount of water separates (about 2 hours). After cooling it was washed with water and then with 10% sodium bicarbonate solution. The solvent was distilled off under reduced pressure. The remaining end-product after distillation over a 15 cm Vigreux column gave 221 g (85%) 3,5,5-trimethylhexanoic acid-2'-ethylhexyl ester as a colorless oil of medium viscosity; B.P. (1.3 mbar)=118°–123° C.

$d_4°^{20°}$: 0.8582 $n_D^{20°}$: 1.4365

EXAMPLE 4

3,5,5-trimethylhexanoic acid-3,5,5-trimethylhexyl ester

The preparation from 3,5,5-trimethylhexanoic acid and 3,5,5-trimethylhexanol was analogous to Example 3; colorless liquid of medium viscosity; B.P. (1.3 mbar=134°–138° C.

$d_4°^{20°}$: 0.8547 $n_D^{20°}$: 1.4371

EXAMPLE 5

3,5,5-trimethylhexanoic acid-isodecyl ester (isomeric mixture)

The preparation from 3,5,5-trimethylhexanoic acid and isodecyl alcohol (mixture of methyl branched primary decanols from Hoechst) was analogous to Example 3; colorless liquid of medium viscosity; B.P. (1.3 mbar)= 148°–154° C.

$d_4°^{20°}$: 0.8596 $n_D^{20°}$: 1.4401

EXAMPLE 6

3,5,5-trimethylhexanoic acid-isotridecyl ester (isomeric mixture)

Preparation according to Example 3 from 3,5,5-trimethylhexanoic acid and isotridecyl alcohol (mixture of methyl branched primary tridecanols from Hoechst); colorless liquid of medium viscosity;

$d_4°^{20°}$: 0.8622 $n_D^{20°}$: 1.4450

EXAMPLE 7

3 5 5 trimethylhexanoic acid-isooctadecyl ester 3,5,5-trimethylhexanoic acid and isooctadecanol were added in the same way as Example 3; colorless liquid of medium viscosity. $d_4°^{20°}$: 0.8559 $n_D^{20°}$: 1.4490

EXAMPLE 8

Preparation of "isooctanoic acid"-methylester 2 g concentrated sulfuric acid were added to a solution of 32 g (1 mol) methanol and 144 g (1 mol) "isooctanoic acid" (isomeric mixture from Ruhrchemie A. G. Oberhausen) in 200 ml toluene and heated to boiling with hater separation until the equimolar amount of water separates (about 2 hours). After cooling it was washed with water and then with 10% sodium bicarbonate solution. The solvent was distilled off under reduced pressure. The remaining end-product after distillation over a 15 cm Vigreux column gave 150 g (95%) isooctanoic acid methylester as an easily mobile liquid with a fruity smell.
B.P.$_1$=58°–63° C. $d_4°^{20°}$: 0.8805 $n_D^{20°}$: 1.4175
FIG. 1: gas chromatogram

EXAMPLE 9

Preparation of isooctanoic acid-2-ethyl-hexylester 2 g concentrated sulfuric acid were added to a solution of 130 g (1 mol) 2-ethylhexanol and 144 g (1 mol) "isooctanoic acid" (isomeric mixture from Ruhrchemie A. G., Oberhausen) in 300 ml toluene and heated to boiling with water separation until the equimolar amount of water separates (about 2 hours). After cooling it was washed with water and then with 10% sodium bicarbonate solution. The remaining end-product gave after distillation over a 15 cm Vigreux column 230 g (90%) isooctanoic acid-2-ethyl-hexylester as a colorless oil of medium viscosity.
B.P.$_1$=110°–117° C. $d_4°^{20°}$: 0.8645 $n_D^{20°}$: 1.4367
The product is an isomeric mixture; FIG. 2: gas chronatogram. Mass spectra (CC/SS coupling) of main isomers 6a, 6a and 6f: FIG. 3.

EXAMPLE 10

Density and refraction of some isooctanoic acid-esters
isooctanoic acid-3,5,5-trimethylhexylester preparation analogous to Example 9; colorless liquid
$d_4^{20°}$: 0.8603 $n_D^{20°}$: 1.4369
isooctanoic caid-isodecylester
preparation analogous to Example 9 ; colorless liquid
$d_4^{20°}$: 0.8651 $n_D^{20°}$:1.4409

Isooctanoic acid-tridecylester preparation analogous to Example 9; colorless liquid
$d_4^{20°}$: 0.8667 $n_D^{20°}$: 1.4460 isooctanoic acid-isooctadecylester
preparation analogous to Example 9; colorless liquid
$d_4^{20°}$: 0.8559 $n_D^{20°}$: 1.4490

EXAMPLE 11

Determination of spreadability

For the time being 0.1 ml isooctanoic acid-2-ethyl-hexyl ester (6a–h) and the mixtures 1a,b were laid down in spots by a pipette in the middle of a circular filter paper (diameter= 110 mm, weight 0.81 g; Schleicher & Schull type 597). The substances distribute themselves by capillary forces. After 20 minutes storage (horizontal) at room temperature, with the paper supported entirely to the edges, the almost circular surfaces, become transparent by absorbtion of the substance (s), were planimetrically determined.

| paraffin oil | 19.8 cm² |
|---|---|
| PCL-liquid (1a,b) | 25.1 cm² |
| 2-ethylhexanoic acid-2'-ethylhexylester | 36.7 cm² |
| 2-ethylhexanoic acid-3,5,5-trimethylhexyl ester | 34.8 cm² |
| 2-ethylhexanoic acid-isodecylester | 27.3 cm² |
| 2-ethylhexanoic acid-isotridecyl ester | 24.2 cm² |
| 2-ethylhexanoic acid-isooctadecyl ester | 19.9 cm² |
| 3,5,5-trimethylhexanoic acid-2-ethylhexyl ester | 38.8 cm² |
| 3,5,5-trimethylhexanoic acid-3,5,5-trimethyl-hexyl ester | 31.2 cm² |
| 3,5,5-trimethylhexanoic acid-isodecyl ester | 33.4 cm² |
| 3,5,5-trimethylhexanoic acid-isotridecyl ester | 26.6 cm² |
| 3,5,5-trimethylhexanoic acid-isooctadecyl ester | 23.7 cm² |
| isooctanoic acid-2-ethylhexyl ester | 58.0 cm² |
| isooctanoic acid-3,5,5-trimethylhexyl ester | 26.5 cm² |
| isooctanoic acid-isodecyl ester | 30.2 cm² |
| isooctanoic acid-isotridecyl ester | 28.7 cm² |
| isooctanoic acid-isooctadecyl ester | 20.2 cm² |

The spreadability of the branch-chain isooctanoic acid esters according to the invention attain or surpass those of paraffin oil or the marketed products 1a,b.

EXAMPLE 12

| Sun-screen oil | |
|---|---|
| paraffin oil 5° K. | 50 |
| isopropylmyristate | 25 |
| multiple branched esters A | 22 |
| p-methoxy-cinnamic acid-octylester | 2 |
| perfume oil | 1 |
| | 100 |

The oil soobtained can presently be applied directly to the skin or as an aerosol-spray.

EXAMPLE 13

| Day cream | |
|---|---|
| glycerine monostearate/sodium stearate | 11.2 |
| isopropylmyristate | 3.0 |
| multiple branched esters A | 2.0 |
| p-hydroxybenzoic acid-ethylester | 0.3 |
| sorbitol F | 3.0 |
| water | 80.0 |
| perfume oil | 0.5 |
| | 100.0 |

A soft, "gentle" skin cream with good stability and good absorption power was obtained by emulsification at 60°–70° C.

EXAMPLE 14

| Soap base | |
|---|---|
| paraffin gel | 4.4 |
| anhydrous lanoline | 4.4 |
| sorbitane-sesquioleate | 2.6 |
| palmitic acid-cetyl ester | 2.2 |
| lanoline alcohol | 1.8 |
| oleic acid-decylester | 5.7 |
| stearic acid | 0.9 |
| butylhydroxytoluene | 0.1 |
| p-hydroxybenzoic acid-ethylester | 0.3 |
| multiple unsaturated esters A | 6.0 |
| magnesium sulfate | 0.5 |
| 1,2-propane diol | 3.0 |
| water | 67.6 |
| perfume oil | 0.5 |
| | 100.0 |

The soap base obtained by emulsifying at 60°–70° C. possessed a very good lifting power.

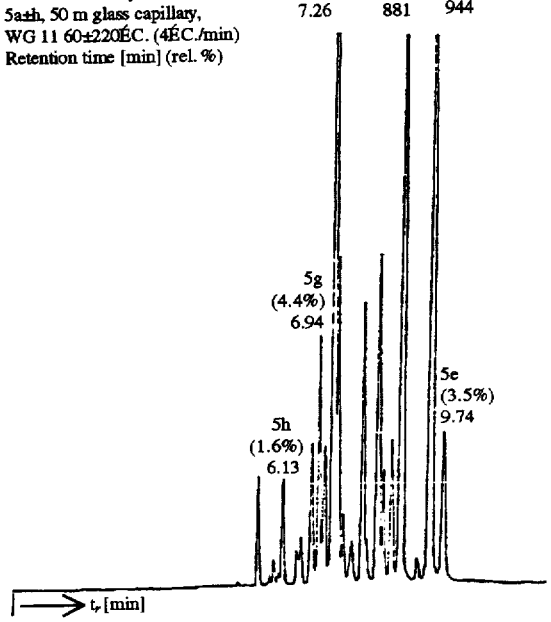

FIG 1: GC Methylester 5a±h, 50 m glass capillary, WG 11 60±220ÉC. (4ÉC./min) Retention time [min] (rel. %)

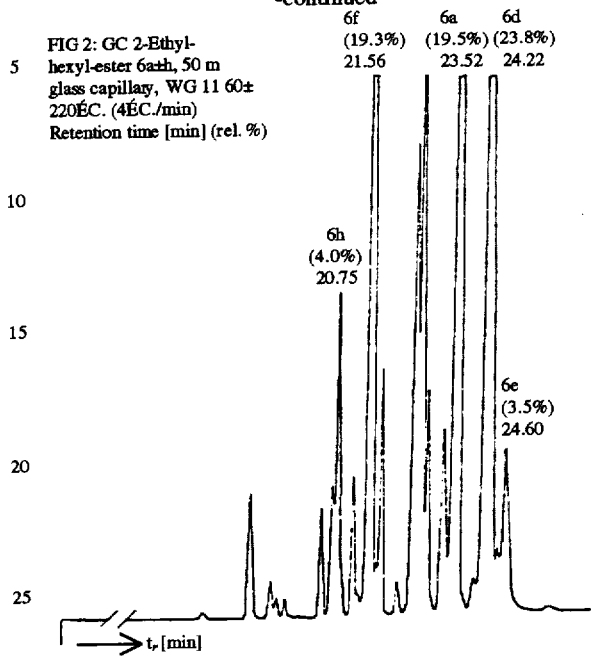

FIG 2: GC 2-Ethyl-hexyl-ester 6a±h, 50 m glass capillary, WG 11 60± 220ÉC. (4ÉC./min) Retention time [min] (rel. %)

We claim:
1. A cosmetic composition which comprises an ester derived from 2-ethylhexanol and 2-ethylhexanoic acids and a cosmetic agent.

* * * * *